(12) United States Patent
Nowakowski et al.

(10) Patent No.: US 6,590,103 B2
(45) Date of Patent: Jul. 8, 2003

(54) PROCESS FOR PREPARING ALKANESULFONYL PYRIDINES

(75) Inventors: Jolanta Nowakowski, Old Saybrook, CT (US); Dieter Haag, Fribourg (CH)

(73) Assignees: Pfizer, Inc., New York, NY (US); Pfizer Products, Inc., Groton, CT (US)

( * ) Notice: Subject to any disclaimer, the term of this patent is extended or adjusted under 35 U.S.C. 154(b) by 0 days.

(21) Appl. No.: 10/259,155

(22) Filed: Sep. 27, 2002

(65) Prior Publication Data

US 2003/0092914 A1 May 15, 2003

Related U.S. Application Data

(60) Provisional application No. 60/325,648, filed on Sep. 28, 2001.

(51) Int. Cl.$^7$ .................... C07D 213/71; C07D 213/77
(52) U.S. Cl. ................ 546/295; 546/294; 546/297
(58) Field of Search ................ 546/295, 294, 546/297

(56) References Cited

U.S. PATENT DOCUMENTS 6,506,779 B1 * 1/2003 Cheng et al. ............... 514/341

* cited by examiner

Primary Examiner—Charanjit S. Aulakh
(74) Attorney, Agent, or Firm—SScully, Scott, Murphy & Presser

(57) ABSTRACT

A process for preparing alkanesulfonyl pyridines of the formula 1:

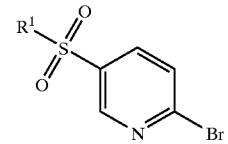

is disclosed, wherein $R^1$ is as defined herein. The compounds of formula 1 are useful in the preparation of pyridyl-substituted pyrazoles used in the treatment and alleviation of inflammation and other inflammation associated disorders.

22 Claims, No Drawings

PROCESS FOR PREPARING ALKANESULFONYL PYRIDINES

CROSS REFERENCE TO RELATED APPLICATIONS

The present application claims benefit of U.S. Provisional Application No. 60/325,648 filed Sep. 28, 2001.

BACKGROUND OF THE INVENTION

This invention relates to a process for the preparation of alkanesulfonyl pyridine derivatives having the formula 1

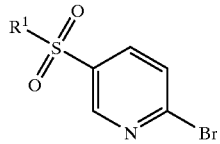

which are useful as intermediates in the synthesis of pyrazole compounds having the formula 5:

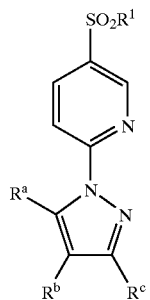

wherein $R^1$ is unsubstituted $(C_1-C_6)$alkyl; $R^6$ is phenyl optionally substituted by 1–3 substituents independently selected from the group consisting of halo, hydroxy, cyano, mercapto, $(C_1-C_6)$alkyl, $(C_2-C_6)$alkenyl. $(C_1-C_6)$alkoxy, —$OCF_3$, $(C_1-C_6)$alkyl-S—, $(C_1-C_6)$alkyl-S(=O)—, $(C_1-C_6)$alkyl-$SO_2$—, amino, $(C_1-C_6)$alkylamino, di[$(C_1-C_6)$alkyl]amino, $H_2$N-(C=O)—, $(C_1-C_6)$alkyl-NH-(C=O)—and formyl; $R^b$ is hydrogen, halo or $(C_1-C_6)$alkyl; and $R^c$ is $(C_1-C_6)$alkyl optionally substituted with from one to three halo atoms.

The compounds of formula 5 ("the active compounds") are useful in the treatment or alleviation of inflammation and other Inflammation associated disorders, such as arthritis, neurodegeneration and colon cancer, in mammals, preferably humans, dogs, cats or livestock. It Is believed that the active compounds inhibit the biosynthesis of prostaglandins by intervention of the action of the enzyme cyclooxygenase on arachidonic acid.

Compounds of formula 5 and other processes for preparing alkanesulfonyl pyridine derivatives are disclosed in co-pending U.S. application Ser. No. 09/724,446, filed Nov. 28, 2000, which is herein incorporated by reference in its entirety. The PCT International Patent Application corresponding to Ser. No. 09/724,446 was published on Jun. 7, 2001 as WO 01/40216. In application 09/724,446 (and WO 01/40216), the sulfonyl pyridine is prepared according to a two-step process involving a first step of forming a sulfide by either nucleophilic substitution using e.g., alkylsulfide or methylation of a mercapto pyridine followed by a second step which Is oxidation of the sulfide to a sulfonyl group.

In the present invention, the alkyl sulfonyl group $R^1$-$SO_2$— is added in a single step to the metallated pyridine (i.e., the Grignard reaction product), thereby avoiding the necessity of an oxidation step from a sulfide. In particular, applicants found that the use in step (b) of alkyl sulfonylating reagents such as alkanesulfonyl halides or alkanesulfonyl anhydrides, which are poor electrophiles compared to, e.g., disulfides (see, Wang et al. (2000) Tet. Lett 41:4335–4338), unexpectedly provided the alkane sulfonyl pyridine selectively and in high yield. It is also worth noting that the alkyl sulfonylating reagents such as those disclosed herein are inexpensive and thus particularly suited for commercial production of the compound of formula 1 and upon further modification, production of compounds of formula 5. Finally, the present invention allows both step (a), metallation, and step (b), alkyl sulfonylation, to be carried out at non-cryogenic temperatures, i.e., above −20° C. Accordingly, the present invention provides a direct and regioselective route to the 5-(alkanesulfonyl)-2-bromo-pyridine.

SUMMARY OF THE INVENTION

The present invention relates to a process for preparing a compound of formula 1:

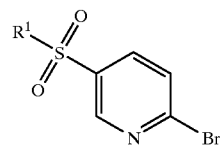

which comprises the steps of:
(a) reacting a compound of formula 2

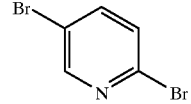

with a Grignard reagent; and
(b) reacting the product of step (a) with an $(C_1-C_6)$alkyl sulfonylating reagent;
wherein $R^1$ is unsubstituted $(C_1-C_6)$alkyl.

In an embodiment of the invention, $R^1$ is unsubstituted $(C_1-C_3)$alkyl. In a preferred embodiment of the invention, $R^1$ is methyl. In a preferred embodiment of the invention $R^1$ is methyl and the alkyl sulfonylating reagent is a methyl sulfonylating reagent.

In another embodiment of the invention, the Grignard reagent is a linear or branched $(C_1-C_{10})$alkyl magnesium halide, i.e., a compound of the formula RMgX, wherein R is linear or branched $(C_1-C_{10})$alkyl and X Is halide. In a preferred embodiment of the invention, the Grignard reagent is a $(C_1-C_4)$alkyl magnesium halide, e.g., methylmagnesium halide, ethylmagnesium halide, propylmagesium halide, isopropylmagnesium halide, butylmagnesium halide or tert-butylmagnesium halide. In a particularly preferred embodiment of the Invention, the Grignard reagent is isopropylmagnesium chloride.

In another embodiment of the invention, step (a) is carried out in a solvent selected from the group consisting of diethyl ether, tetrahydrofuran ("THF"), glyme (1,2-dimethoxyethane) or diglyme (bis(2-methoxyethyl) ether). In a preferred embodiment of the invention, the solvent in step (a) is THF.

In another embodiment of the invention, step (a) is carried out at a temperature of from about −20° C. to about room temperature (about 20° C.–25° C. ). In another embodiment of the invention, step (a) is carried out at a temperature of from about −20° C. to about 10° C. In another embodiment of the invention, step (a) is carried out for a period of from about 30 minutes to about 4 hours, preferably for about 45 minutes.

In another embodiment of the invention, the alkyl sulfonylating agent is a $(C_1$–$C_6)$alkanesulfonyl halide or a $(C_1$–$C_6)$alkanesulfonic anhydride. In a preferred embodiment of the invention, the alkyl sulfonylating agent is an alkanesulfonyl halide of the formula $R^1SO_2X$, wherein X is chloro or fluoro. In a preferred embodiment of the invention, the alkanesulfonyl halide is unsubstituted $(C_1$–$C_3)$ alkanesulfonyl halide. In a more preferred embodiment of the invention, the alkanesulfonyl halide is methanesulfonyl fluoride or methanesulfonyl chloride. In a particularly preferred embodiment of the invention, the alkanesulfonyl halide is methanesulfonyl chloride. In another preferred embodiment of the invention, the alkyl sulfonylating agent is an alkanesulfonic anhydride of the formula $(R^1SO_2)_2O$. In a more preferred embodiment of the invention, the alkanesulfonic anhydride is unsubstituted $(C_1$–$C_3)$alkanesulfonic anhydride. In a particularly preferred embodiment of the invention, the alkanesulfonic anhydride is methanesulfonic anhydride.

In another embodiment of the invention, step (b) is carried out in THF.

In another embodiment of the invention, the process further comprises preparing a compound of formula 3

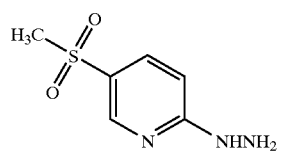

3 by hydrazinolysis of the compound of formula 1 in the presence of an amine, in a suitable solvent. In an embodiment of the invention, the hydrazinolysis is carried out using a hydrazine such as hydrazine hydrate. In an embodiment of the invention, the amine is selected from the group consisting of triethylamine, diisopropylethylamine, 2,6-lutidine and N,N,N',N'-tetramethylethylenediamine. In a preferred embodiment of the invention, the amine is triethylamine. In another embodiment of the invention, the suitable solvent for hydrazinolysis is selected from the group consisting of water, dichloromethane, dichloroethane and toluene. In a preferred embodiment of the invention, the solvent is water.

The compounds prepared by the processes of the present invention that are basic in nature, e.g., compounds of formula 3, are capable of forming a wide variety of different salts with various Inorganic and organic acids. The acid addition salts of the base compounds prepared by the processes of this invention are readily prepared by treating the base compound with a substantially equivalent amount of the chosen mineral or organic acid in an aqueous solvent medium or in a suitable organic solvent. Upon careful evaporation of the solvent, the desired solid salt is readily obtained. The desired salt can also be precipitated from a solution of the free base in an organic solvent by adding to the solution an appropriate mineral or organic acid.

In another embodiment of the invention, the process further comprises treating the compound of formula 3 with an acid in a suitable solvent. In a preferred embodiment of the invention, the acid is hydrochloric acid. In an embodiment of the invention, the acid addition salt of the compound of formula 3 prepared according to the process of the invention Is the hydrochloride salt.

In another .embodiment of the invention, the hydrazinolysis is carried out at a temperature between room temperature and about 100° C., preferably at about 70° C. In another embodiment of the invention, the hydrazinolysis is carried out for a period of from about 3 hours to about 24 hours, preferably about 5 hours.

The present invention also relates to the hydrochloride addition salt of the compound of formula 3 prepared by the process of this invention.

It is to be noted that the term "mixture", as used herein, unless otherwise indicated, is used without regard to the state of dispersion of the components thereof.

The phrase "organic solvent" as used herein, unless otherwise indicated, means a non-aqueous solvent or mixture of non-aqueous solvents.

In a preferred embodiment of the processes described herein, the reaction is carried out at about atmospheric pressure. In this application, the term "atmospheric pressure" means a pressure within the normal range of meteorologic atmospheric pressure for a particular altitude, while the term elevated pressure means a pressure above atmospheric pressure. In another embodiment of the processes described herein, the reaction is carried out at elevated pressure.

Unless otherwise indicated, the term "alkyl" as referred to herein, as well as the alkyl moieties of other groups referred to herein (e.q., alkoxy), may be linear or branched (such as methyl, ethyl, n-propyl, isopropyl, n-butyl, iso-butyl, secondaty-butyl, tertiary-butyl), and they may also be cyclic (e.q., cyclopropyl, or cyclobutyl); optionally substituted by 1 to 3 suitable substituents as defined below such as fluoro, chloro, trifluoromrethyl, $(C_1$–$C_6)$alkoxy, $(C_6$–$C_{10})$aryloxy, trifluoromethoxy, difluoromethoxy or $(C_1$–$C_6)$alkyl. The phrase "each of said alkyl" as used herein refers to any of the preceding alkyl moieties within a group such alkoxy, alkenyl or alkylamino.

Unless otherwise indicated, the terms "halo" and "halogen" are used herein interchangeably to mean fluoro, chloro, bromo or iodo, or fluorine, chlorine, bromine or iodine, respectively, while the term "halide" is used herein to refer to the fluoride, chloride, bromide or iodide anions.

As used herein, the term "halo-substituted alkyl" refers to an alkyl radical as described above substituted with one or more halogens including, but not limited to, chloromethyl, dichloromethyl, fluoromethyl, difluoromethyl, trifluoromethyl, 2,2,2-trichloroethyl, and the like; optionally substituted by 1 to 3 suitable substituents as defined below such as fluoro, chloro, trifluoromethyl, $(C_1$–$C_6)$alkoxy, $(C_6$–$C_{10})$aryloxy, trifluoromethoxy, difluoromethoxy or $(C_1$–$C_6)$alkyl.

As used herein, the term "alkenyl" means straight or branched chain unsaturated radicals of 2 to 6 carbon atoms, including, but not limited to ethenyl, 1-propenyl, 2-propenyl (allyl), iso-propenyl, 2-methyl-1-propenyl, 1-butenyl, 2-butenyl, and the like; optionally substituted by 1 to 3 suitable substituents as defined below such as fluoro, chloro, trifluoromethyl, $(C_1$–$C_6)$alkoxy, $(C_6$–$C_{10})$aryloxy, trifluoromethoxy, difluoromethoxy or $(C_1$–$C_6)$alkyl.

As used herein, the term "alkynyl" is used herein to mean straight or branched hydrocarbon chain radicals of 2 to 6 carbon atoms having one triple bond including, but not limited to, ethynyl, propynyl, butynyl, and the like; optionally substituted by 1 to 3 suitable substituents as defined below such as fluoro, chloro, trinfluoromethyl, ($C_1$-$C_6$) alkoxy, ($C_6$-$C_{10}$)aryloxy, trifluoromethoxy, difluoromethoxy or ($C_1$-$C_6$)alkyl.

As used herein, the term "alkoxy" refers to O-alkyl groups, wherein alkyl is as defined above.

As used herein, the term "alkoxycarbonyl" refers to an alkoxy radical as described above connected to a carbonyl group (>C=O), which, in turn, serves as the point of attachment.

The phrase "pharmaceutically acceptable salt(s)", as used herein, unless otherwise indicated, includes salts of acidic or basic groups which may be present in the compounds of the present invention. The compounds prepared by the processes of the present invention that are basic in nature are capable of forming a wide variety of salts with various inorganic and organic acids. The acids that may be used to prepare pharmaceutically acceptable acid addition salts of such basic compounds of the present invention are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tarlrate, pantothenate, bitartrate, ascorbate, succinate, maleate, gentisinate, fumarale, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. The compounds prepared by the processes of the present invention that include an amino moiety may form pharmaceutically acceptable salts with various amino acids, in addition to the acids mentioned above.

The present invention includes processes for preparing a compound of formula 1 wherein one or more hydrogen, carbon, nitrogen or other atoms are replaced by isotopes thereof. Such compounds are useful as diagnostic tools and in metabolic, pharmacokinetic and binding studies. Examples of isotopes that can be utilized in the processes of the invention include isotopes of hydrogen, carbon, nitrogen, oxygen, sulfur, fluorine and chlorine, as $^2$H, $^3$H, $^{13}$C, $^{14}$C, $^{15}$N, $^{18}$O, $^{17}$O, $^{35}$S, $^{18}$F, and $^{36}$Cl, respectively. Processes of the present invention which utilize the aforementioned isotopes and/or other isotopes of other atoms are within the scope of this invention. Certain isotopically-labelled compounds prepared by the processes of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds prepared by the processes of this invention can generally be prepared by carrying out the procedures disclosed in the Schemes and/or in the Examples below, by substituting a readily available isotopically labelled reagent for a non-isotopically labelled reagent.

DETAILED DESCRIPTION OF THE INVENTION

The process of the present invention may be carried out according to Scheme 1 below and the description that follows.

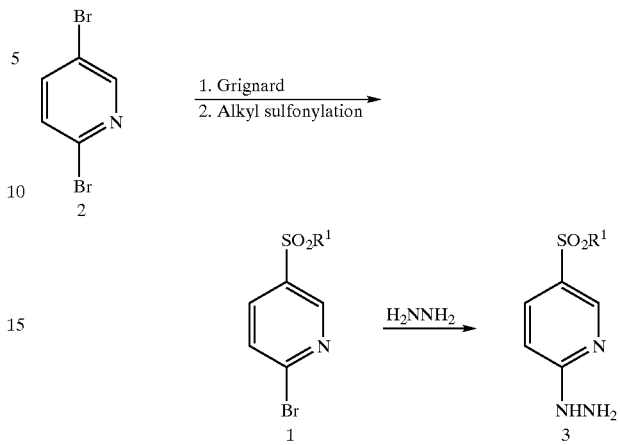

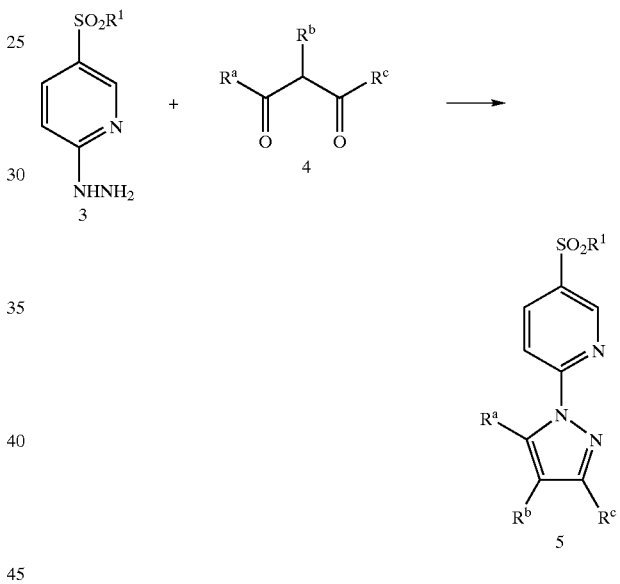

Schemes 1 and 2 given above are illustrative only and are described in further detail below and in the Examples further hereinbelow. Substituents $R^1$ and $R^a$–$R^c$ in Schemes 1 and 2 are as follows: $R^1$ is ($C_1$–$C_6$)alkyl, $R^a$ is phenyl optionally substituted by 1–3 substituents independently selected from the group consisting of halo, hydroxy, cyano, mercapto, ($C_1$–$C_6$)alkyl, ($C_2$–$C_6$)alkenyl, ($C_1$–$C_6$)alkoxy, —OCF$_3$, ($C_1$–$C_6$)alkyl-S—, ($C_1$–$C_6$)alkyl-S(=O)—, ($C_1$–$C_6$)alkyl-SO$_2$—, amino, ($C_1$–$C_6$)alkylamino, di[($C_1$–$C_6$)alkyl]amino, $H_2$N-(C=O)—, ($C_1$–$C_6$)alkyl-NH-(C=O)—and formyl; $R^b$ is hydrogen, halo or ($C_1$–$C_6$)alkyl; and $R^c$ is ($C_1$–$C_6$)alkyl optiona substituted with from one to three halo atoms.

The first stage in Scheme 1 is a direct alkylsulfonylation of 2,5-bromopyridine. The compound of formula 2,2,5-dibromopyridine, is (1) treated with a Grignard reagent and then (2) reacted with an alkyl sulfonylating agent to yield the compound of formula 1. The Grignard reagent, i.e., RMgX, wherein R is ($C_1$–$C_6$)alkyl and X is halo, is preferably a propyl or butyl Grignard reagent, e.g., propylmagesium halide or isopropylmagnesium halide, most preferably isopropylmagnesium chloride. The metallation (Grignard) reaction is preferably carried out at a temperature between about −20° C. to about room temperature for a period of from about 0.5 hours to about 4 hours, preferably for about 45 minutes. Suitable solvents for the Grignard reaction include, but are not limited to, diethyl ether, tetrahydrofuran ("THF"), glyme (1,2-dimethoxyethane) or diglyme (bis(2-methoxyethyl) ether). Preferably, the solvent is THF.

The alkyl sulfonylating agent is preferably an alkanesulfonyl halide (i.e., $R^1SO_2X$, wherein X is halo) or an alkanesulfonic anhydride (i.e., $(R^1SO2)2O)$. Preferably, the alkanesulfonyl halide is unsubstituted $(C_1-C_3)$ alkanesulfonyl halide. More preferably, the alkyl sulfonylating agent is methanesulfonyl fluoride or methanesulfonyl chloride. Particularly preferred is methanesulfonyl chloride. A preferred alkanesulfonic anhydride is unsubstituted $(C_1-C_3)$alkanesulfonic anhydride. A particularly preferred alkanesulfonic anhydride is methanesulfonic anhydride.

The second, optional stage is hydrazinolysis of the compound of formula 1 to yield the compound of formula 3. The compound of formula 1 is reacted with a hydrazine, such as hydrazine hydrate, in the presence of an amine such as triethylamine, diisopropylethylamine, 2,6-lutidine, N,N,N', N'-tetramethylethylenediamine, preferably in triethylamine in the presence of a solvent such as water, dichloromethane, dichloroethane, toluene, preferably in water, at a temperature between room temperature and 100° C., preferably at about 70° C. for a period of from about 3 hours to about 24 hours, preferably 5 hours, to afford a compound of formula 3.

Scheme 2 shows the use of the compound of formula 3 in the preparation of a compound of formula 5. Processes for preparing the compound of formula 5 are disclosed in co-pending U.S. aplication Ser. No. 09/724,446, filed Nov. 28, 2000, which is herein incorporated by reference in its entirety. The PCT International Patent Application corresponding to Serial No. 09/724,446 was published on Jun. 7, 2001 as WO 01/40216. Processes for preparing the compound of formula 5 are also disclosed in the copending U.S. provisional application "Process for preparing heterocycloalkylsulfonyl pyrazole derivatives" by David Ripin, Michael Castaldi and Dennis Bourassa, which has been filed concurrently with the present application, which is herein incorporated by reference in its entirety.

The active compounds prepared using compounds of formula 1 and formula 3 prepared by the processes of this invention, may be administered through oral, parenteral, topical, or rectal routes in the treatment or alleviation of inflammation and other inflammation associated disorders, such as arthritis, neurodegeneration and colon cancer, in mammals, preferably humans, dogs, cats or livestock.

In general, the active compounds are most desirably administered in dosages ranging from about 0.2 mg per kg body weight per day (mg/kg/day) to about 200 mg/kg/day in single or divided doses (i.e., from 1 to 4 doses per day), although variations will necessarily occur depending upon the species, weight and condition of the subject being treated and the particular route of administration chosen. However, a dosage level that is in the range of about 4 mg/kg/day to about 50 mg/kg/day is most desirably employed. Variations may nevertheless occur depending upon the species of mammal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

The active compounds may be administered alone or in combination with pharmaceutically acceptable carriers or diluents by the routes previously indicated, and such administration may be carried out in single or multiple doses. More particularly, the active compounds may be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the active compounds are present in such dosage forms at concentration levels ranging from about 5.0% to about 70% by weight. Numerous examples of acceptable carriers, diluents, excipients, disintegrants, lubricating agents, sweetening and flavoring agents, coloring matter or dyes, emulsifying agents, suspending agents, diluents, buffers, creams, jellies, gels, pastes, patches, ointments, etc. useful in the preparation of pharmaceutical compositions and formulations are known in the art, see, Reminoton's Pharmaceutical Sciences, Mack Publishing Company, Easton, Pa., 18th Edition, Gennaro, ed. (1990), pages 1545–1580. The preparation of all these compositions under sterile conditions is readily accomplished by standard pharmaceutical techniques will known to those skilled in the art.

For administration to animals other than humans, such as cattle or domestic animals, such as dogs or cats, the active compounds may be administered in the feed of the animals or orally as a drench composition.

The active compounds may also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The active compounds may also be coupled with soluble polymers as targetable drug carriers. Such polymers can include polyvinylpyrrolidone, pyran copolymer, polyhydroxypropylmethacrylamide phenyl, polyhydroxyethylaspartamide-phenol, or polyethyleneoxide-polylysine substituted with palmitoyl residues. Furthermore, the active compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross-linked or amphipathic block copolymers of hydrogels.

The following Examples further illustrate the process and intermediates of the present invention. Example 1 (i)–(iii) represent preferred embodiments of the invention, however, it is to be understood that the present invention is not limited to the specific details of the Examples provided below.

EXAMPLE 1

2-Bromo-5-(Methanesulfonyl)-Pyridine (i) To a solution of 2,5-dibromopyridine (50 g, 211 mmol) in tetrahydrofuran (175 mL) at 0° C. was added 2.0 M isopropylmagnesium chloride (274 mmol) at a rate to maintain the temperature below B° C. The reaction mixture was stirred at 0° C. for 45 minutes, then cooled to −15° C. A solution of methanesulfonyl chloride (32.2 g, 281 mmol) in tetrahydrofuran (40 mL) was added to the reaction mixture at such a rate to maintain the temperature below 5° C. The reaction mixture was allowed to warm to room temperature and then quenched with waler (500 mL) and tert-butylmethylether (300 mL). The layers were separated the aqueous layer was extracted twice with tert-butylmethylether (2×200 mL). The combined organic extracts were washed with water (200 mL) and concentrated. The crude product was crystallized from toluene (110 mL), the solids were filtered to afford 29.4 g (59% yield) of 2-bromo-5-(methanesulfonyl)-pyridine. $^1$H NMR (300 MHz, CDCI$_3$) δ3.13 (s, 3H), 7.73 (d, J=8.3 Hz, 1H), 8.07 (dd, J$_1$=8.3 Hz, J$_2$=2.7 Hz, 1H), 8.91 (d, J=2.5 Hz, 1H).

(ii) In the reaction described above in (i), the use of methanesulfonyl fluoride as the sulfonylating agent provides the product with 53% yield.

(iii) In the reaction described above in (i), the use of methanesulfonic anhydride, i.e, (CH$_3$SO$_2$)$_2$O, as the sulfonylating agent provides the product with 50% yield.

EXAMPLE 2

2-Hydrazino-5-(Methanesulfonyl)-pyridine

A suspension of 2-bromo-5-(methanesulfonyl)-pyridine (27.5 g, 116 mmol), triethylamine (14.7 g. 145 mmol), and hydrazine hydrate (7.26 g, 145 mmol) in water (205 ml) was heated to 70° C. The reaction mixture became homogenous before the product started to precipitate out of this mixture (after 90 minutes). The reaction mixture was stirred at 70° C. for total of 5 hours and then was allowed to cool to room temperature and stirred for 18 hours. The precipitated product was collected by filtration, dried and triturated with hot ethanol to afford 2-hydrazino-5-(methanesulfonyl)-pyridine in 86% yield. $^1$H NMR (300 MHz, CDCI$_3$) δ3.12 (s, 3H), 4.44 (br s, 2H), 6.80 (br d, J=8.7 Hz. 1H), 7.81 (dd. J$_1$=9.0 Hz, J$_2$=2.4 Hz, 1H), 8.38 (d, 2.3 Hz, 1H), 8.57 (br s, 1H).

What is claimed is:

1. A process for preparing a compound of formula 1

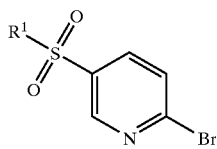

which comprises the steps of:
 (a) reacting a compound of formula 2

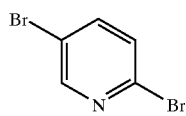

with a Grignard reagent; and
 (b) reacting the product of step (a) with a (C$_1$–C$_6$)alkyl sulfonylating reagent;
wherein R$^1$ is unsubstituted (C$_1$–C$_6$)alkyl.

2. The process of claim 1, wherein R$^1$ is methyl.

3. The process of claim 1, wherein the Grignard reagent is a linear or branched (C$_1$–C$_{10}$)alkyl magnesium halide.

4. The process of claim 3, wherein the Grignard reagent is a linear or branched (C$_1$–C$_4$)alkyl magnesium halide.

5. The process of claim 4, wherein the Grignard reagent is isopropyl magnesium chloride.

6. The process of claim 1, wherein step (a) is carried out in a solvent selected from the group consisting of diethyl ether, THF, 1,2-dimethoxyethane or bis(2-methoxyethyl) ether.

7. The process of claim 6, wherein the solvent is THF.

8. The process of claim 1, wherein the alkyl sulfonylating agent is an alkanesulfonyl halide or an alkanesulfonyl anhydride.

9. The process of claim 8, wherein the alkyl sulfonylating agent is an alkanesulfonyl halide of the formula R$^1$SO$_2$X, wherein X is fluoro or chloro.

10. The process of claim 9, wherein the alkane sulfonyl halide is methanesulfonyl chloride.

11. The process of claim 8, wherein the alkyl sulfonylating agent is an alkanesulfonyl anhydride of the formula (R$^1$SO$_2$)$_2$O.

12. The process of claim 11, wherein the alkane sulfonyl anhydride is methanesulfonic anhydride.

13. The process of claim 1, wherein step (b) is carried out in THF.

14. The process of claim 1, which further comprises preparing a compound of formula 3

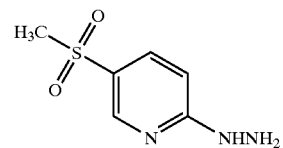

by hydrazinolysis of a compound of formula 1 in the presence of an amine, in a suitable solvent.

15. The process of claim 14, wherein the hydrazinolysis is carried out using hydrazine hydrate.

16. The process of claim 14, wherein the amine is selected from the group consisting of triethylamine, diisopropylethylamine, 2,6-lutidine and N,N,N',N'-tetramethylethylenediamine.

17. The process of claim 16, wherein the amine is triethylamine.

18. The process of claim 14, wherein the solvent is selected from the group consisting of water, dichloromethane, dichloroethane and toluene.

19. The process of claim 18, wherein the solvent is water.

20. The process of claim 14, which further comprises treating the compound of formula 3 with an acid in a suitable solvent.

21. The process of claim 20, wherein the acid is hydrochloric acid.

22. The hydrochloric acid addition salt of the compound of formula 3, prepared by the process of claim 21.

* * * * *